(12) United States Patent
Wenning

(10) Patent No.: US 6,342,576 B1
(45) Date of Patent: Jan. 29, 2002

(54) URETHANIZED β-HYDROXYALKYLAMIDE COMPOUND, A PROCESS FOR PREPARING IT AND ITS USE FOR PREPARING POWDER COATING MATERIALS

(75) Inventor: Andreas Wenning, Nottuln (DE)

(73) Assignee: Degussa-Huels AG, Frankfurt (DE)

( * ) Notice: Subject to any disclaimer, the term of this patent is extended or adjusted under 35 U.S.C. 154(b) by 0 days.

(21) Appl. No.: 09/577,598

(22) Filed: May 25, 2000

(30) Foreign Application Priority Data

Jun. 4, 1999 (DE) .......................................... 199 25 543

(51) Int. Cl.⁷ .............................. C08J 3/06; C08K 3/26; C08L 75/00; C08G 18/00; C08G 18/32

(52) U.S. Cl. ................. 528/44; 252/182.2; 252/182.22; 252/182.24; 252/182.26; 524/507; 524/539; 524/589; 524/590; 525/123; 525/127; 525/440; 525/453; 525/455; 528/44; 528/60; 528/65; 528/59; 528/85; 564/123; 564/152; 564/153; 564/160; 564/163; 564/167

(58) Field of Search ............................... 528/44, 60, 65, 528/85, 59; 524/539, 589, 590, 507; 525/123, 127, 440, 455, 453; 252/182.2, 182.22, 182.24, 182.26; 564/123, 152, 153, 160, 163, 167

(56) References Cited

FOREIGN PATENT DOCUMENTS

| EP | 0 322 834 | 7/1989 |
| EP | 0 698 629 | 2/1996 |
| EP | 0 789 043 | 8/1997 |

*Primary Examiner*—Patrick D. Niland
(74) *Attorney, Agent, or Firm*—Oblon, Spivak, McClelland, Maier & Neustadt, P.C.

(57) ABSTRACT

A urethanized β-hydroxyalkylamide compound, a process for its preparation, and powder coating materials containing them.

23 Claims, No Drawings

URETHANIZED β-HYDROXYALKYLAMIDE COMPOUND, A PROCESS FOR PREPARING IT AND ITS USE FOR PREPARING POWDER COATING MATERIALS

BACKGROUND OF THE INVENTION

1. Field of the Invention

The invention relates to urethanized β-hydroxyalkylamide compounds, to a process for preparing them, to their use for preparing highly reactive powder coating materials, and to the powder coating materials themselves.

2. Description of the Background

Powder coating materials based on triglycidyl isocyanurate (TGIC) and acid functional polyesters give corrosion-resistant and weather-stable powder coatings. EP 0 536 085 describes, however, how the preparation of TGIC in solid form necessitates expensive processes or a relatively great, and therefore likewise expensive, purification effort. Moreover, TGIC is classified by the European Community as a category II mutagen (to be regarded as inducing heritable genetic defects) and as of May 31, 1998 has had to be labeled as toxic.

Toxicologically acceptable crosslinkers which are also more reactive include hydroxyalkylamides. In patents U.S. Pat. Nos. 4,076,917 and 4,101,606, the hydroxyalkylamides are combined with polymers having at least one carboxyl or anhydride function, in particular with polyacrylates, to form powder coating materials. EP 0 322 834 describes heat-curing powder coating materials which are composed of polyesters containing acid groups and of β-hydroxyalkylamides. These coatings with β-hydroxyalkylamide crosslinkers are highly weather-stable, very flexible, hard and chemical-resistant. For numerous applications, such as in the sanitation industry or in the coating of laboratory equipment, the chemical resistance is not, however, sufficient.

It was therefore the object of the present invention to find novel crosslinkers which in combination with carboxyl-containing polymers can be processed to powder coating materials which give coatings extremely resistant to chemicals.

SUMMARY OF THE INVENTION

It has surprisingly been found that urethanized β-hydroxyalkylamide compounds constitute outstanding crosslinkers and, in combination with acidic polymers in powder coating materials, bring about a massively increased chemical resistance without detriment to the flexibility, hardness, reactivity, or weathering stability.

The present invention therefore provides urethanized β-hydroxyalkylamide compounds synthesized from the components A) from 65 to 96% by weight of β-hydroxyalkylamide and B) from 4 to 35% by weight of a nonaromatic polyisocyanate having an NCO functionality $\geq 2$, the urethanized β-hydroxyalkylamide compounds carrying hydroxyl groups terminally and having a functionality $\geq 2$.

DETAILED DESCRIPTION OF THE INVENTION

The invention preferably provides urethanized β-hydroxyalkylamide compounds wherein the β-hydroxyalkylamide A) has the formula

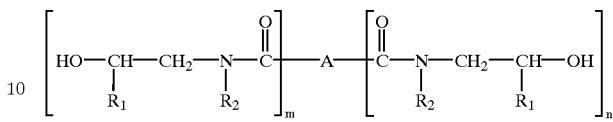

in which $R_1$ is hydrogen or a $C_1$–$C_5$ alkyl group, $R_2$ is hydrogen, a $C_1$–$C_5$ alkyl group or

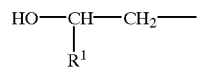

wherein $R_1$ is as defined above, and A is a chemical bond or, a monovalent or polyvalent organic group selected from saturated, unsaturated and aromatic hydrocarbon groups, and substituted hydrocarbon groups, having 2 to 20 carbon atoms, m is 1 or 2, n is from 0 to 2 and m+n is at least 2.

With particular preference, these compounds of the invention have a functionality of four or more.

The invention further provides for the use of the urethanized β-hydroxyalkylamide compounds to prepare transparent or pigmented, outdoor-resistant powder coating materials having high reactivity and hardness, excellent gloss and very good chemical resistance, prepared from the urethanized β-hydroxyalkylamide compound and carboxyl-containing polymers and also from the adjuvants customary in the chemistry of powder coatings, such as pigments, fillers, leveling agents, devolatilizers, catalysts if desired, and other additives, for example.

The invention also provides transparent and pigmented powder coating materials comprising the urethanized β-hydroxyalkylamide compounds of the invention.

The β-hydroxyalkylamides A) are known in principle and are described, for example, in U.S. Pat. Nos. 4,076,917; 4,101,606; EP 0 322 834 and EP 0 473 380. The structure can be described as follows:

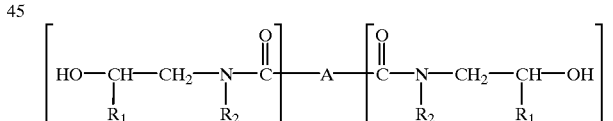

in which $R_1$ is hydrogen or $C_1$–$C_5$ alkyl, $R_2$ is hydrogen, $C_1$–$C_5$ alkyl or

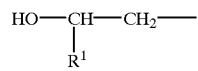

where $R_1$ is as defined above, and A is a chemical bond or a monovalent or polyvalent organic group derived from saturated, unsaturated or aromatic hydrocarbon groups, including substituted hydrocarbon groups of 2 to 20 carbon atoms, m is 1 or 2, n is from 0 to 2 and m+n is at least 2.

The nonaromatic polyisocyanate B) having an NCO functionality $\geq 2$ can be any aliphatic, (cyclo)aliphatic, cycloaliphatic or heterocyclic polyisocyanate having at least two isocyanate groups, or a mixture thereof. Polyisocyanates of this kind are mentioned, for example, in Houben-Weyl, Methoden der Organischen Chemie, Volume 14/2, page 61 ff. and in J. Liebigs Annalen der Chemie, Volume 562, pages 75 to 136. Representative examples of the polyisocyanates are aliphatic isocyanates such as alkylene isocyanates, e.g., ethylene diisocyanate, propylene diisocyanate, tetramethylene diisocyanate, pentamethylene diisocyanate, 2-methylpentamethylene 1,5-diisocyanate (MPDI), hexamethylene diisocyanate (HDI), trimethylhexamethylene 1,6-diisocyanate (TMDI), especially the 2,2,4 and the 2,4,4 isomer, and technical-grade mixtures of both isomers, decamethylene diisocyanate and dodecamethylene diisocyanate, and also cycloalkylene isocyanates, e.g. 1,3-cyclopentyl diisocyanate, 1,2-cyclohexyl diisocyanate, 1,4-cyclohexyl diisocyanate, ω,ω'-diisocyanato-1,4-methylcyclohexane, ω,ω'-diisocyanato-1,3-dimethylcyclohexane, 1-methyl-2,4-diisocyanatocyclohexane, 4,4'-methylenebis(cyclohexyl isocyanate), norbornane diisocyanate (NBDI) and 3,3,5-trimethyl-1-isocyanato-3-isocyanatomethylcyclohexane (isophorone diisocyanate, IPDI). Advantageous polyisocyanates are those obtainable by reacting polyisocyanates with themselves via isocyanate groups; especially isocyanurates, which come about through the reaction of three isocyanate groups. Mixtures of diisocyanates and isocyanurates, especially of 2-methylpentamethylene 1,5-diisocyanate, 2,2,4-trimethylhexamethylene 1,6-diisocyanate, 2,4,4-trimethylhexamethylene 1,6-diisocyanate, norbornane diisocyanate, isophorone diisocyanate, the isocyanurate of 2-methylpentamethylene 1,5-diisocyanate, the isocyanurate of hexamethylene diisocyanate or the isocyanurate of isophorone diisocyanate, are particularly advantageous. The polyisocyanates may likewise include biuret groups or allophanate groups.

The invention additionally provides a process for preparing urethanized hydroxyalkylamide compounds, which comprises reacting from 65 to 96% by weight of at least one β-hydroxyalkylamide A) with from 4 to 35% by weight of at least one nonaromatic polyisocyanate B), the urethanized β-hydroxyalkylamide compounds carrying hydroxyl groups terminally and having a functionality≧2.

The urethanized β-hydroxyalkylamide compounds of the invention can be prepared in a solvent. Preferably, however, they are prepared in bulk—that is, without solvent. For this purpose, the β-hydroxyalkylamide A) is introduced initially and the polyisocyanate B) is added. The reaction can be monitored by determining the NCO number and is over after from 30 minutes to 3 hours. Known methods and technologies are used for cooling, comminuting and bagging.

The present invention further provides for the use of the urethanized β-hydroxyalkylamide compounds of the invention to prepare transparent or pigmented weathering-resistant powder coating materials of high reactivity and hardness and excellent gloss.

The invention additionally provides transparent or pigmented powder coating materials which comprise the urethanized β-hydroxyalkylamide compounds of the invention and carboxyl-containing polymers and also the adjuvants customary in the chemistry of powder coatings, such as pigments, fillers, leveling agents, devolatilizers, catalysts if desired, and other additives, for example. In comparison to β-hydroxyalkylamide crosslinkers containing no urethane groups, the coatings prepared from the powder coating materials of the invention are notable for a greatly improved chemical resistance.

Appropriate co-reactants for the urethanized β-hydroxyalkylamide compounds of the invention, for the preparation of powder coating materials, are carboxyl-containing polymers. The polymers used can be addition polymers, polycondensates and polyaddition compounds. In principle, it is possible to use any polymer which contains at least two carboxyl groups and melts at at least 60° C. For the purposes of the invention, particular preference is given to polycarboxyl polyesters and polycarboxyl polyacrylates.

The carboxyl-containing polymers are preferably polyester polycarboxylic acids which are prepared from polyols and polycarboxylic acids and/or derivatives thereof. The melting point of these acidic polyesters is situated within a range from 60 to 160° C., preferably from 80 to 120° C.; their acid number varies from 10 to 150 mg KOH/g, preferably from 30 to 60 mg KOH/g. The OH numbers should be below 10 mg KOH/g.

The polyester polycarboxylic acids to be used in accordance with the invention are prepared using polycarboxylic acids, such as, for example, oxalic acid, adipic acid, 2,2,4 (2,4,4)-trimethyladipic acid, azelaic acid, sebacic acid, decanedicarboxylic acid, dodecanedicarboxylic acid, fumaric acid, phthalic acid, isophthalic acid, terephthalic acid, trimellitic acid and pyromellitic acid. Examples of polyols used for the acidic polyesters are the following: ethylene glycol, 1,2- and 1,3-propanediol, 1,2-, 1,3-, 1,4- and 2,3-butanediol, 1,5-pentanediol, 3-methyl-1,5-pentanediol, neopentyl glycol, 1,12-dodecanediol, 2,2,4(2, 4,4)-trimethyl-1,6-hexanediol, trimethylolpropane, glycerol, pentaerythritol, 1,4-bishydroxylmethylcyclohexane, cyclohexane-1,4-diol, diethylene glycol, triethylene glycol and dipropylene glycol. It is of course also possible to react hydroxyl-containing polyesters, which are prepared by known processes from polycarboxylic acids and polyols, with polycarboxylic acids and/or polycarboxylic anhydrides to give the polyester polycarboxylic acids.

Suitable carboxyl-functional acrylate polymers possess an acid number of from 10 to 150 mg KOH/g and a melting point of from 60 to 160° C. and are prepared by copolymerizing a monomer mixture consisting of a) from 0 to 70 parts by weight of methyl (meth)acrylate, b) from 0 to 60 parts by weight of (cyclo)alkyl esters of acrylic and/or methacrylic acid having 2 to 18 carbon atoms in the alkyl or cycloalkyl radical, c) from 0 to 90 parts by weight of vinylaromatic compounds, and d) from 0 to 60 parts by weight of olefinically unsaturated carboxylic acids, the sum of the parts by weight of components a) to d) being 100.

The monomers b) are preferably (cyclo)alkyl esters of acrylic or methacrylic acid having 2 to 18 carbon atoms in the (cyclo)alkyl radical. Examples of suitable, or preferably suitable, monomers b) are ethyl (meth)acrylate, n-propyl (meth)acrylate, isopropyl (meth)acrylate, n-butyl (meth) acrylate, isobutyl (meth)acrylate, tert-butyl (meth)acrylate, 2-ethylhexyl (meth)acrylate, cyclohexyl methacrylate, neopentyl methacrylate, isobornyl methacrylate, 3,3,5-trimethylcyclohexyl methacrylate and stearyl methacrylate.

Examples of suitable monomers c) are styrene, vinyl toluene and ethyl styrene. Examples of d) are acrylic and methacrylic acid, which are also used with preference, and also crotonic acid, itaconic acid, fumaric acid, maleic acid, and citraconic acid.

The copolymers can be prepared by copolymerizing the exemplified monomers a) to d) by customary free-radical addition polymerization processes, such as, for example, solution, emulsion, bead or bulk polymerization.

The monomers are copolymerized at temperatures from 60 to 160° C., preferably from 80 to 150° C., in the presence of free-radical initiators and, if desired, of molecular weight regulators.

The carboxyl-functional acrylate copolymers are prepared in inert solvents. Examples of suitable solvents are aromatic compounds, such as benzene, toluene and xylene; esters, such as ethyl acetate, butyl acetate, hexyl acetate, heptyl acetate, methylglycol acetate, ethylglycol acetate, and methoxypropyl acetate; ethers, such as tetrahydrofuran, dioxane, and diethylene glycol dimethyl ether; ketones, such as acetone, methyl ethyl ketone, methyl isobutyl ketone, methyl n-amyl ketone, and methyl isoamyl ketone; or any desired mixtures of such solvents.

The copolymers can be prepared continuously or batchwise. Normally, the monomer mixture and the initiator are metered continuously at a uniform rate into a polymerization reactor and at the same time the corresponding amount of polymer is taken off continuously. In this way, preferably, it is possible to prepare copolymers which are virtually uniform chemically. Chemically near-uniform copolymers can also be prepared by running the reaction mixture at constant rate into a stirred vessel, without taking off the polymer.

Alternatively, a portion of the monomers can be introduced as an initial charge, by way of example, in solvents of the stated type, and the remaining monomers and auxiliaries can be introduced, separately or together, into this initial charge at the reaction temperature. In general, the polymerization is conducted under atmospheric pressure but can also be carried out at pressures of up to 25 bar. The initiators are used in amounts of from 0.05 to 15% by weight, based on the total amount of the monomers.

Suitable initiators include customary free-radical initiators, examples being aliphatic azo compounds, such as azodiisobutyronitrile, azobis-2-methylvaleronitrile, 1,1'-azobis-1-cyclohexanenitrile and 2,2'-azobisisobutyric alkyl esters; symmetrical diacyl peroxides, such as acetyl, propionyl or butyryl peroxide, for example, bromo-, nitro-, methyl- or methoxy-substituted benzoyl peroxides, lauryl peroxides; symmetric peroxydicarbonates, e.g., tert-butyl perbenzoate; hydroperoxides, such as tert-butyl hydroperoxide, cumin hydroperoxide; and dialkyl peroxides, such as dicumyl peroxide, tert-butyl cumyl peroxide, or di-tert-butyl peroxide. To regulate the molecular weight of the copolymers it is possible to use customary regulators during the preparation. Examples that may be mentioned include mercaptopropionic acid, tert-dodecyl mercaptan, n-dodecyl mercaptan, and diisopropylxanthogen disulfide. The regulators can be added in amounts of from 0.1 to 10% by weight, based on the total amount of the monomers.

The copolymer solutions obtained from the copolymerization can then be supplied without further working up to the degassing or devolatilization process, in which the solvent is removed, for example, in a devolatilizing extruder or spray drier at from about 120 to 160° C. under a vacuum of from 100 to 300 mbar and the copolymers to be used in accordance with the invention are obtained.

As polycarboxyl compounds, it is of course also possible to use mixtures of two or more substances.

The mixing proportion of the carboxyl-containing polymers and of the urethanized β-hydroxyalkylamide compound of the invention is generally chosen such that the ratio of carboxyl groups to hydroxide groups is from 0.6:1 to 1.6:1.

It is normally not necessary to add a catalyst in order to increase the gelling rate of heat-curable powder coating materials. If the acidic polymer contains an aliphatic resin in which residues of 1,4-cyclohexanedicarboxylic acid (CHDA) and of the 2,2,4,4-tetramethyl-1,3-cyclobutanediol ester or residues of 1,4-CHDA and of hydrogenated bisphenol A are present, then it is possible, as described in WO 95/01466, that catalysts comprising $C_1$–$C_{18}$ zinc, aluminum or titanium carboxylate salts, or aluminum oxides or zinc oxides, have an accelerating effect. They are used in amounts of from 0.03 to 1.0% by weight, based on the total amount of powder.

For the preparation of powder coating materials, the urethanized β-hydroxyalkylamide compounds of the invention are mixed with the appropriate carboxyl-containing polymers and, if desired, catalysts and also pigments and customary auxiliaries such as fillers, devolatilizers and leveling agents. All of the ingredients of the powder coating material are homogenized in the melt. This can be done in suitable equipment, such as beatable compounders, for example, but preferably by extrusion, in the course of which the temperature ought not to exceed an upper limit of from 130 to 140° C. After cooling to room temperature and appropriate comminution, the extruded mass is ground to give the ready-to-spray powder. The application of this powder to appropriate substrates can be done by the known techniques, such as, for example, by electrostatic or tribostatic powder spraying, unassisted fluidized-bed sintering, or electrostatic fluidized-bed sintering. Following the application of the powder, the coated workpieces are cured by heating for from 60 to 5 minutes at a temperature of from 150 to 220° C.

Having generally described this invention, a further understanding can be obtained by reference to certain specific examples which are provided herein for purposes of illustration only and are not intended to be limiting unless otherwise specified.

EXAMPLES

A Preparation of the Urethanized β-hydroxyalkylamide Compound of the Invention

A1 β-Hydroxyalkylamide A)

PRIMID XL-552 (OH number: 682 mg KOH/g, melting point: 125° C., EMS-Chemie AG) was used as the β-hydroxyalkylamide A).

A2 Polyisocyanate B)

VESTANAT® T 1890 (isocyanurate of IPDI, NCO number 17.1%, CREANOVA Spezialchemie GmbH) and isophorone diisocyanate (IPDI, NCO number 37.8%, CREANOVA Spezialchemie GmbH) were used as polyisocyanate B).

A3 Urethanized β-hydroxyalkylamide compounds

General Solvent-free Preparation Procedure

The β-hydroxyalkylamide A) is charged to a steel pot and melted at a temperature of about 125° C. The polyisocyanate B) is metered in. Following a reaction period of about 3 hours, the product is cooled and comminuted.

The physical and chemical characteristics of the inventive process products, and the molar compositions, are collated in Table 1.

Table 1: Urethanized β-hydroxyalkylamides in comparison with β-hydroxyalkylamide

| | Composition | | | Characteristics | |
| --- | --- | --- | --- | --- | --- |
| Example No. | PRIMID XL-552 [% by wt.] | T 1890 [% by wt.] | IPDI [% by wt.] | OH number [mg KOH/g] | m.p. [° C.] |
| A 3.1 | 72.9 | 27.1 | — | 435 | 93–98 |
| A 3.2 | 80.2 | 19.8 | — | 501 | 104–110 |

-continued

| | Composition | | | Characteristics | |
|---|---|---|---|---|---|
| | PRIMID | T 1890 | | | |
| Example No. | XL-552 [% by wt.] | [% by wt.] | IPDI [% by wt.] | OH number [mg KOH/g] | m.p. [° C.] |
| A 3.3 | 84.4 | 15.6 | — | 539 | 109–113 |
| A 3.4 | 73.9 | 24.8 | 1.3 | 441 | 90–95 |
| A 3.5 Comparison | 100 | — | — | 682 | 125 |

B Polymer

The polymer used was the acidic polyester Grilesta P 7617 from EMSChemie AG (acid number 35 mg KOH/g, Tg 61° C., viscosity at 200° C. 3500 mPa·s).

C Powder Coating Materials

General Preparation Procedure

The comminuted products, i.e., urethanized β-hydroxyalkylamide compound, acidic polyester, leveling agent masterbatch, and catalysts if desired, are intimately mixed, together if appropriate with white pigment, in an edge runner mill and the mixture is then homogenized in a twin-screw extruder from Berstorff at temperatures of up to 130° C. After cooling, the extrudate is fractionated and ground with a pinned-disk mill to a particle size <100 μm. The powder prepared in this way is applied to degreased and optionally pretreated iron panels using an electrostatic powder spraying unit at 60 kV and the coated panels are then baked in a circulating-air oven at temperatures between 150 and 220° C.

Leveling Agent Masterbatch 10 percent by weight of the leveling agent—a commercially customary copolymer of butyl acrylate and 2-ethylhexyl acrylate—are homogenized in the melt in the corresponding polyester, and the melt is comminuted after it has solidified.

The abbreviations in the table below have the following meanings:

| | | |
|---|---|---|
| CT | = Coat thickness in μm | |
| HK | = König hardness (sec) | (DIN 53 157) |
| EI | = Erichsen indentation | (DIN 53 156) |
| CH | = Cross-hatch test | (DIN 53 151) |
| GG 60° angle | = Gardner gloss measurement | (ASTM-D 5233) |
| Imp. Rev. | = Impact reverse in inch.lb | |
| MEK test | = Methyl ethyl ketone test, in strokes | |

(a cotton pad soaked with MEK and then pressed is guided over the coating using a hammer with a weight of 1 kg, until the coating becomes matt.)

TABLE 2

| Pigmented powder coating materials | | | | | |
|---|---|---|---|---|---|
| Example C Formulation | 1 | 2 | 3 | 4 | 5 Comparison |
| Crosslinker acc. to A3 | 6.86 | 6.53 | 6.09 | 7.35 | 4.84 |
| Table 1 | (1) | (2) | (3) | (4) | (5) |
| Polyester acc. to B | 93.14 | 93.47 | 93.91 | 92.65 | 95.16 |
| Notes: | 35% by weight TiO₂ (white pigment), 1.0% by weight Resiflow PV 88, 0.3% by weight benzoin, COOH/OH ratio = 1:1 | | | | |

TABLE 2-continued

| Pigmented powder coating materials | | | | | |
|---|---|---|---|---|---|
| Example C Formulation | 1 | 2 | 3 | 4 | 5 Comparison |
| Coating data | | | | | |
| CT | 50–64 | 70–94 | 62–96 | 55–70 | 81–101 |
| HK | 174 | 192 | 195 | 192 | 193 |
| CH | 0 | 0 | 0 | 0 | 0 |
| GG 60° angle | 92 | 92 | 93 | 91 | 92 |
| EI | >10 | >10 | >10 | >10 | >10 |
| Imp. Rev. | >80 | >80 | >80 | >80 | >80 |
| MEK test | 32 | 50 | 50 | 46 | 16 |
| Curing: | 200° C./10 minutes | | | | |

The disclosure of German priority application, No. 19925543.1, filed Jun. 4, 1999, is hereby incorporated by reference.

What is claimed is:

1. A urethanized β-hydroxyalkylamide compound synthesized from the components
   A) from 65 to 96% by weight of β-hydroxyalkylamide and
   B) from 4 to 35% by weight of a nonaromatic polyisocyanate having an NCO functionality>2,
   wherein the urethanized β-hydroxyalkylamide compound carries hydroxyl groups terminally and has a functionality>2.

2. The urethanized β-hydroxyalkylamide compound as claimed in claim 1, wherein the β-hydroxyalkylamide A) has the formula

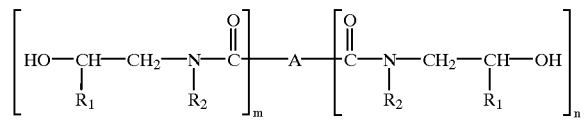

in which $R_1$ is hydrogen or a $C_1$–$C_5$ alkyl group, $R_2$ is hydrogen, a $C_1$–$C_{15}$ alkyl group or

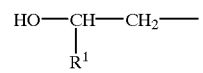

wherein $R_1$ is as defined above, and A is a chemical bond or a monovalent or polyvalent organic group selected from aliphatic saturated, aliphatic unsaturated, and aromatic hydrocarbon groups, wherein the hydrocarbon groups are unsubstituted or substituted, and wherein the hydrocarbon groups have 2 to 20 carbon atoms when aliphatic, and 6 to 20 carbon atoms when aromatic, m is 1 or 2, n is from 0 to 2 and m+n is at least 2.

3. The urethanized βhydroxyalkylamide compound as claimed in claim 1, which has a functionality>4.

4. The urethanized β-hydroxyalkylamide compound as claimed in claim 2, which has a functionality>4.

5. The urethanized β-hydroxyalkylamide compound as claimed in claim 1, wherein said polyisocyanate B) comprises at least one compound selected from the group consisting of aliphatic, (cyclo)aliphatic, cycloaliphatic and heterocyclic polyisocyanates having at least two isocyanate groups.

6. The urethanized β-hydroxyalkylamide compound as claimed in claim 2, wherein said polyisocyanate B) comprises at least one compound selected from the group consisting of aliphatic, (cyclo)aliphatic, cycloaliphatic and heterocyclic polyisocyanates having at least two isocyanate groups.

7. The urethanized β-hydroxyalkylamide compound as claimed in claim 3, wherein said polyisocyanate B) comprises at least one compound selected from the group consisting of aliphatic, (cyclo)aliphatic, cycloaliphatic and heterocyclic polyisocyanates having at least two isocyanate groups.

8. The urethanized β-hydroxyalkylamide compound as claimed in claim 4, wherein, said polyisocyanate B) comprises at least one compound selected from the group consisting of aliphatic, (cyclo)aliphatic, cycloaliphatic and heterocyclic polyisocyanates having at least two isocyanate groups.

9. The urethanized β-hydroxyalkylamide compound as claimed in claim 1, wherein said polyisocyanate B) comprises at least one compound selected from the group consisting of ethylene diisocyanate, propylene diisocyanate, tetramethylene diisocyanate, pentamethylene diisocyanate, 2-methylpentamethylene 1,5-diisocyanate (MPDI), hexamethylene diisocyanate (HDI), trimethylhexamethylene 1,6-diisocyanate (TMDI), decamethylene diisocyanate, dodecamethylene diisocyanate, 1,3-cyclopentyl diisocyanate, 1,2-cyclohexyl diisocyanate, 1,4-cyclohexyl diisocyanate, ω,ω'-diisocyanto-1,4-methylcyclohexane, ω,ω'-diisocyanato1,3-dimethylcyclohexane, 1-methyl-2,4-diisocyanatocyclohexane, 4,4'-methylenebis(cyclohexyl isocyanate), norbornane diisocyanate (NBDI) and 3,3,5-trimethyl-1-isocyanato-3-isocyanatomethylcyclohexane (isophorone diisocyanate, IPDI).

10. The urethanized β-hydroxyalkylamide compound as claimed in claim 9, wherein said polyisocyanate B) comprises the 2,2,4 isomer, the 2,4,4 isomer, or technical-grade mixtures of both isomers, of TMDI.

11. The urethanized β-hydroxyalkylamide compound as claimed in claim 9, wherein said polyisocyanate B) comprises a mixture of (1) a diisocyanate selected from the group consisting of 2-methylpentamethylene 1,5-diisocyanate, 2,2,4-trimethylhexamethylene 1,6-diisocyanate, 2,4,4-trimethylhexamethylene 1,6-diisocyanate, norbornane diisocyanate, and isophorone diisocyanate, and (2) a isocyanurate selected from the group consisting of the isocyanurate of 2-methylpentamethylene 1,5-diisocyanate, the isocyanurate of hexamethylene diisocyanate and the isocyanurate of isophorone diisocyanate.

12. A process for preparing a urethanized β-hydroxyalkylamide compound, which comprises reacting from 65 to 96% by weight of at least one β-hydroxyalkylamide A) with from 4 to 35% by weight of at least one nonaromatic polyisocyanate B), wherein the urethanized β-hydroxyalkylamide compound carries hydroxyl groups terminally and has a functionality>2.

13. The process for preparing a urethanized β-hydroxyalkylamide compound, as claimed in claim 12, wherein the reaction of the compounds A) and B) takes place without solvent in a batch process.

14. A transparent or pigmented powder coating material which comprises at least one urethanized β-hydroxyalkylamide compound as claimed in claim 1, in combination with a carboxyl-containing polymer, and optionally further auxiliaries and adjuvants.

15. The transparent or pigmented powder coating material as claimed in claim 14, wherein said auxiliaries and adjuvants comprise fillers, leveling agents, devolatilizers or catalysts.

16. The transparent or pigmented powder coating material as claimed in claim 14, which is based on a COOH/OH ratio of from 0.6:1.0 to 1.6:1.0.

17. The transparent or pigmented powder coating material as claimed in claim 16, which is based on a COOH/OH ratio of from 0.8:1.0 to 1.2:1.0.

18. The transparent or pigmented powder coating material as claimed in claim 16, which is based on a COOH/OH ratio of 1:1.

19. The transparent or pigmented powder coating material as claimed in claim 14, which comprises catalyst(s) in a concentration of from 0.03 to 1.0% by weight, based on the total amount of powder coating material.

20. The transparent or pigmented powder coating material as claimed in claim 19, wherein the catalyst(s) are one or more selected from the group consisting of aluminum carboxylate salts, titanium carboxylate salts, aluminum oxides and zinc oxides.

21. The transparent or pigmented powder coating material as claimed in claim 14, wherein the carboxyl-containing polymer is a polycarboxyl polyester or polycarboxyl polyacrylate.

22. The transparent or pigmented powder coating material as claimed in claim 21, wherein the carboxyl-containing polymer is a polycarboxyl polyester having an acid number of from 10 to 150 mg KOH/g and a melting point of from 60 to 160° C.

23. The transparent or pigmented powder coating material as claimed in claim 21, wherein the carboxyl-containing polymer is a polycarboxyl polyacrylate having an acid number of from 10 to 150 mg KOH/g and a melting point of from 60 to 160° C.

* * * * *